United States Patent
Tyson et al.

(10) Patent No.: US 11,659,980 B2
(45) Date of Patent: May 30, 2023

(54) USER INTERFACE WITH DUAL-FUNCTION CONTROL SURFACE FOR POSITIONING MULTIPLE COMPONENTS WITHIN A BODY

(71) Applicant: GYRUS ACMI, INC., Westborough, MA (US)

(72) Inventors: Taylor N. Tyson, Seattle, WA (US); Cassandra R. Saleira, Bothell, WA (US)

(73) Assignee: Gyrus ACMI, Inc., Westborough, MA (US)

(*) Notice: Subject to any disclaimer, the term of this patent is extended or adjusted under 35 U.S.C. 154(b) by 1041 days.

(21) Appl. No.: 16/367,151

(22) Filed: Mar. 27, 2019

(65) Prior Publication Data
US 2020/0305685 A1    Oct. 1, 2020

(51) Int. Cl.
*A61B 18/14*   (2006.01)
*A61B 1/005*   (2006.01)
(Continued)

(52) U.S. Cl.
CPC ........ *A61B 1/0052* (2013.01); *A61B 1/00066* (2013.01); *A61B 18/1492* (2013.01);
(Continued)

(58) Field of Classification Search
CPC .............. A61B 1/0052; A61B 1/00066; A61B 1/00087; A61B 18/1492; A61B 5/6852;
(Continued)

(56) References Cited

U.S. PATENT DOCUMENTS 4,869,259 A    9/1989 Elkins
5,190,541 A  * 3/1993 Abele ................ A61B 18/1442
                                                                606/49
(Continued)

OTHER PUBLICATIONS

International Search Report and Written Opinion rcvd in related application PCT/US2017/023242.

*Primary Examiner* — Michael F Peffley
*Assistant Examiner* — Bo Ouyang
(74) *Attorney, Agent, or Firm* — Schwegman Lundberg & Woessner, P.A.

(57) ABSTRACT

Disclosed embodiments include apparatuses, systems, and methods for positioning electrodes within a body. In an illustrative embodiment, a control handle is selectively engageable with primary and secondary actuators respectively coupled with primary and secondary electrodes. At a first position, the primary and secondary actuators are movably engaged to move in concert to a second position where distal ends of the electrodes extend into a target region. At the second position, the control handle is engaged with the secondary actuator and movable independently of the primary actuator in a first direction to a third position where the distal end of the secondary electrode extends beyond the distal end of the primary electrode. At the third position, the control handle is movably engaged with the primary actuator and movable independently of the secondary actuator in a second direction to a fourth position to partially retract the distal end of the primary electrode.

17 Claims, 10 Drawing Sheets

(51) Int. Cl.
*A61B 1/00* (2006.01)
*A61B 5/00* (2006.01)
*A61B 17/00* (2006.01)
*A61B 18/00* (2006.01)

(52) U.S. Cl.
CPC ......... *A61B 1/00087* (2013.01); *A61B 5/6852* (2013.01); *A61B 2017/00367* (2013.01); *A61B 2018/0091* (2013.01); *A61B 2018/144* (2013.01); *A61B 2018/1475* (2013.01)

(58) Field of Classification Search
CPC .... A61B 2018/0091; A61B 2018/1442; A61B 2018/1475; A61B 2017/00367
See application file for complete search history.

(56) References Cited

U.S. PATENT DOCUMENTS

| | | | |
|---|---|---|---|
| 5,919,202 | A | 7/1999 | Yoon |
| 6,416,510 | B1 | 7/2002 | Altman et al. |
| 6,749,604 | B1 | 6/2004 | Eggers et al. |
| 7,357,798 | B2 | 4/2008 | Sharps et al. |
| 7,419,488 | B2 | 9/2008 | Ciarrocca et al. |
| 8,043,286 | B2 | 10/2011 | Palanker et al. |
| 8,114,071 | B2 | 2/2012 | Woloszko et al. |
| 8,328,837 | B2 * | 12/2012 | Binmoeller ......... A61M 25/104 604/164.01 |
| 8,361,066 | B2 | 1/2013 | Long et al. |
| 9,539,012 | B2 | 1/2017 | Landry et al. |
| 9,888,926 | B2 | 2/2018 | Phan et al. |
| 10,548,661 | B2 * | 2/2020 | Darmos ............. A61B 18/1477 |
| 2002/0091382 | A1 | 7/2002 | Hooven |
| 2003/0028231 | A1 | 2/2003 | Partridge et al. |
| 2003/0083682 | A1 | 5/2003 | Heise |
| 2004/0059328 | A1 | 3/2004 | Daniel et al. |
| 2005/0113827 | A1 | 5/2005 | Dumbauld et al. |
| 2009/0076412 | A1 | 3/2009 | Rioux et al. |
| 2009/0299362 | A1 | 12/2009 | Long et al. |
| 2010/0004723 | A1 | 1/2010 | Foster et al. |
| 2010/0256627 | A1 | 10/2010 | Ma et al. |
| 2010/0324637 | A1 | 12/2010 | Trip et al. |
| 2012/0035474 | A1 | 2/2012 | Deckman et al. |
| 2012/0053485 | A1 | 3/2012 | Bloom |
| 2013/0190609 | A1 | 7/2013 | Fischer, Jr. |
| 2013/0204068 | A1 | 8/2013 | Gnanashanmugam et al. |
| 2013/0226026 | A1 | 8/2013 | Dillard et al. |
| 2013/0310823 | A1 | 11/2013 | Gelfand et al. |
| 2014/0276764 | A1 | 9/2014 | Shuman et al. |
| 2015/0005769 | A1 | 1/2015 | Klink et al. |
| 2016/0015451 | A1 * | 1/2016 | Shikhman ........... A61B 18/1492 606/41 |
| 2018/0206903 | A1 | 7/2018 | Podany |
| 2018/0263686 | A1 * | 9/2018 | Shuman ............. A61B 1/00133 |

* cited by examiner

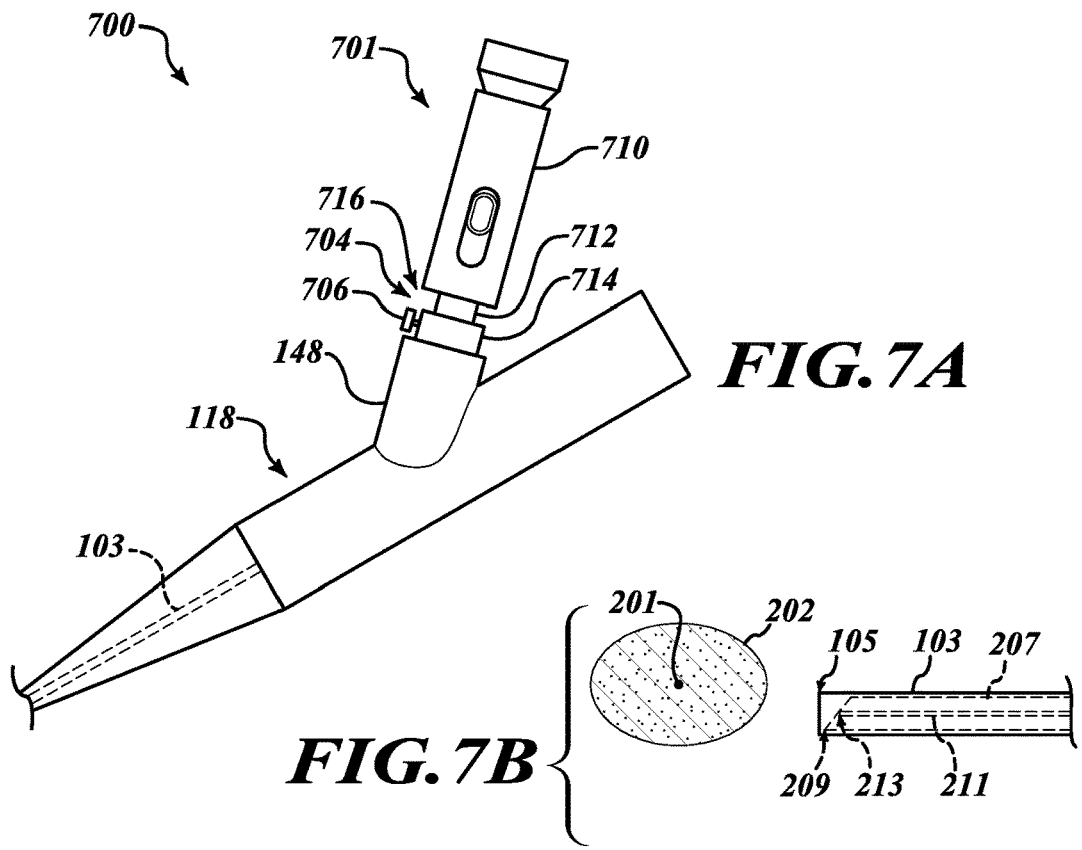
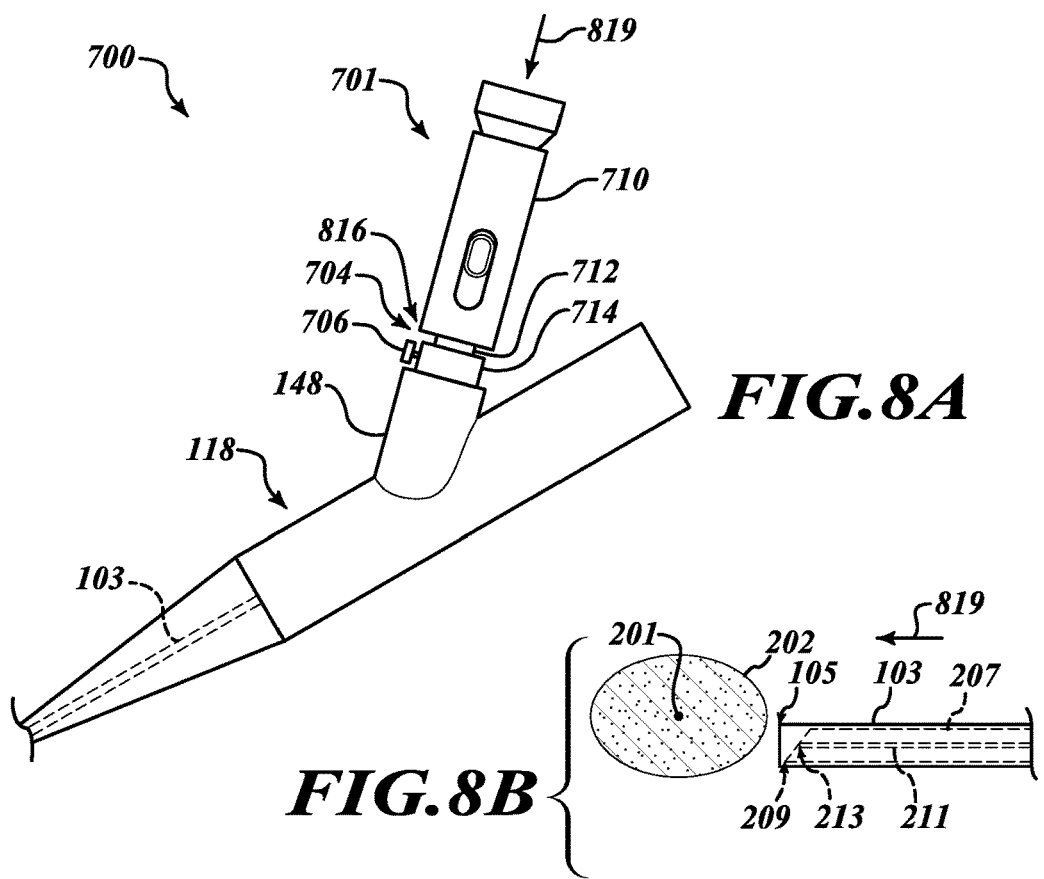

USER INTERFACE WITH DUAL-FUNCTION CONTROL SURFACE FOR POSITIONING MULTIPLE COMPONENTS WITHIN A BODY

FIELD

The present disclosure relates to a user interface and lock features for positioning multiple components within a body.

BACKGROUND

The statements in this section merely provide background information related to the present disclosure and may not constitute prior art.

Inserting and manipulating thin elements within living bodies or other objects allows for ever-improving types of analysis, diagnosis, and treatment of those bodies or objects with minimally invasive techniques. By way of two examples, endoscopic imaging and catherization treatments have enabled evaluation and treatment of numerous internal lesions without invasive surgery.

Electrosurgical techniques also provide for minimally invasive therapies by selectively applying electrical current to selected tissues. Electrosurgical techniques involve extending one or more electrodes through an orifice or a small incision to a desired location within a body, then applying a radio frequency ("RF") electric current to the electrodes to coagulate and/or ablate tissue at that location. Monopolar electrosurgical instruments only entail use of one electrode that interacts with a neutral electrode, which is likewise connected to the body of a patient. A bipolar electrosurgical instrument typically includes a user interface used for positioning two electrodes, which may include a distal electrode and a proximal electrode.

Positioning one or two electrodes at the desired location is an important part of such electrosurgical treatments. Moving and holding electrodes in place, particularly when more than one electrode has to be moved or held independently of another electrode, may present a challenge for the medical personnel directing the treatment. Because positioning one or more electrodes in place may involve adhering to an order of steps, assisting an operator in properly following a sequence also may be important.

SUMMARY

Disclosed embodiments include apparatuses for slidably moving multiple components within a body, systems for treating tissue at a reference point, and methods for moving electrodes into positions for ablative electrical treatment at a reference point.

In an illustrative embodiment, an apparatus includes a housing that is coupled with a sheath that contains a primary electrode and a secondary electrode. The sheath is configured to convey distal ends of the primary electrode and the secondary electrode adjacent to a target region. A primary actuator is operably coupled with the primary electrode. A secondary actuator is operably coupled with the secondary electrode. A control handle is selectively engageable with the primary actuator and the secondary actuator. The primary actuator, the secondary actuator, and the control handle are configured so that, at a first position, the primary actuator and the secondary actuator are movably engaged to move in concert to a second position where the distal ends of the primary electrode and the secondary electrode extend into the target region. At the second position, the control handle is movably engaged with the secondary actuator to be movable independently of the primary actuator in a first direction to a third position where the distal end of the secondary electrode extends beyond the distal end of the primary electrode. At the third position, the control handle is movably engaged with the primary actuator to be movable independently of the secondary actuator in a second direction to a fourth position to partially retract the distal end of the primary electrode away from the distal end of the secondary electrode.

In another illustrative embodiment, a system for treating tissue at a reference point includes a controllable electrical power source configured to selectively provide electrical power between a first pole and a second pole. An electrosurgical apparatus is configured to be inserted into a body to convey a sheath housing a primary electrode electrically coupled with the first pole of the electrical power source and a secondary electrode electrically coupled with the second pole of the electrical power source to a vicinity of a reference point. A user interface includes a housing that is coupled with a sheath that contains a primary electrode and a secondary electrode. The sheath is configured to convey distal ends of the primary electrode and the secondary electrode adjacent to a target region. A primary actuator is operably coupled with the primary electrode. A secondary actuator is operably coupled with the secondary electrode. A control handle is selectively engageable with the primary actuator and the secondary actuator. The primary actuator, the secondary actuator, and the control handle are configured so that, at a first position, the primary actuator and the secondary actuator are movably engaged to move in concert to a second position where the distal ends of the primary electrode and the secondary electrode extend into the target region. At the second position, the control handle is movably engaged with the secondary actuator to be movable independently of the primary actuator in a first direction to a third position where the distal end of the secondary electrode extends beyond the distal end of the primary electrode. At the third position, the control handle is movably engaged with the primary actuator to be movable independently of the secondary actuator in a second direction to a fourth position to partially retract the distal end of the primary electrode away from the distal end of the secondary electrode.

In a further illustrative embodiment, a method includes a user interface operably coupled with a sheath that contains a primary electrode and a secondary electrode being positioned to move a distal end of the sheath adjacent to a target region at a first position. A primary actuator operably coupled with the primary electrode, a secondary actuator operably coupled with the secondary electrode, and a control handle are moved in concert to a second position of the user interface to extend distal ends of the primary electrode and the secondary electrode into the target region. The control handle is moved in a first direction to cause the secondary actuator to move independently of the primary actuator to a third position of the user interface to extend the distal end of the secondary electrode beyond the distal end of the primary electrode. The control handle is moved in a second direction to cause the primary actuator to move independently of the secondary actuator to a fourth position of the user interface to partially retract the distal end of the primary electrode away from the distal end of the secondary electrode.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIGS. 7A and 8A are schematic diagrams of a sheath actuator for positioning a sheath relative to a reference point;

FIGS. 7B and 8B are schematic diagrams of positioning of distal ends of the sheath, a primary electrode, and a secondary electrode relative to a reference point corresponding to positions of the sheath actuator of FIGS. 7A and 8A, respectively;

Figure 20A:
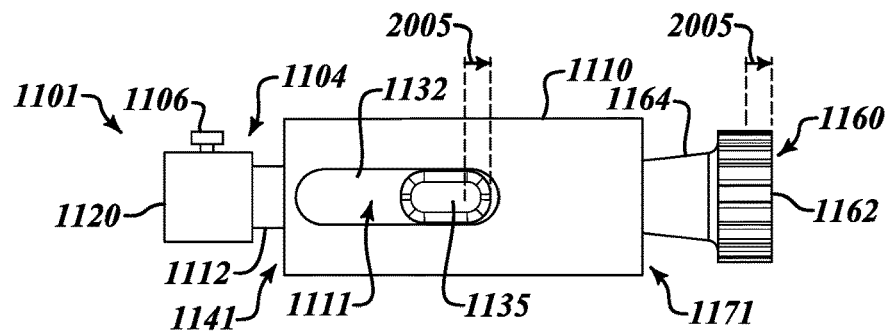
Figure 20B:
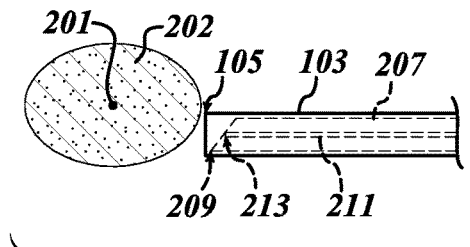
Figure 21A:
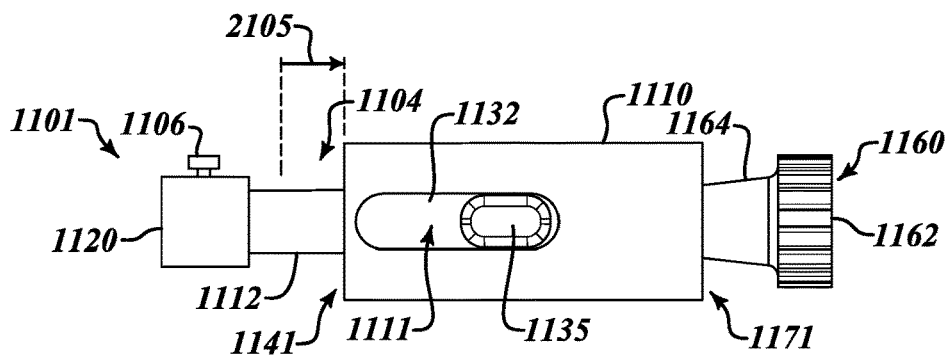
Figure 21B:
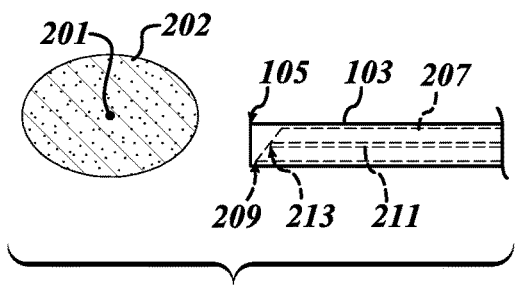
Figure 22:
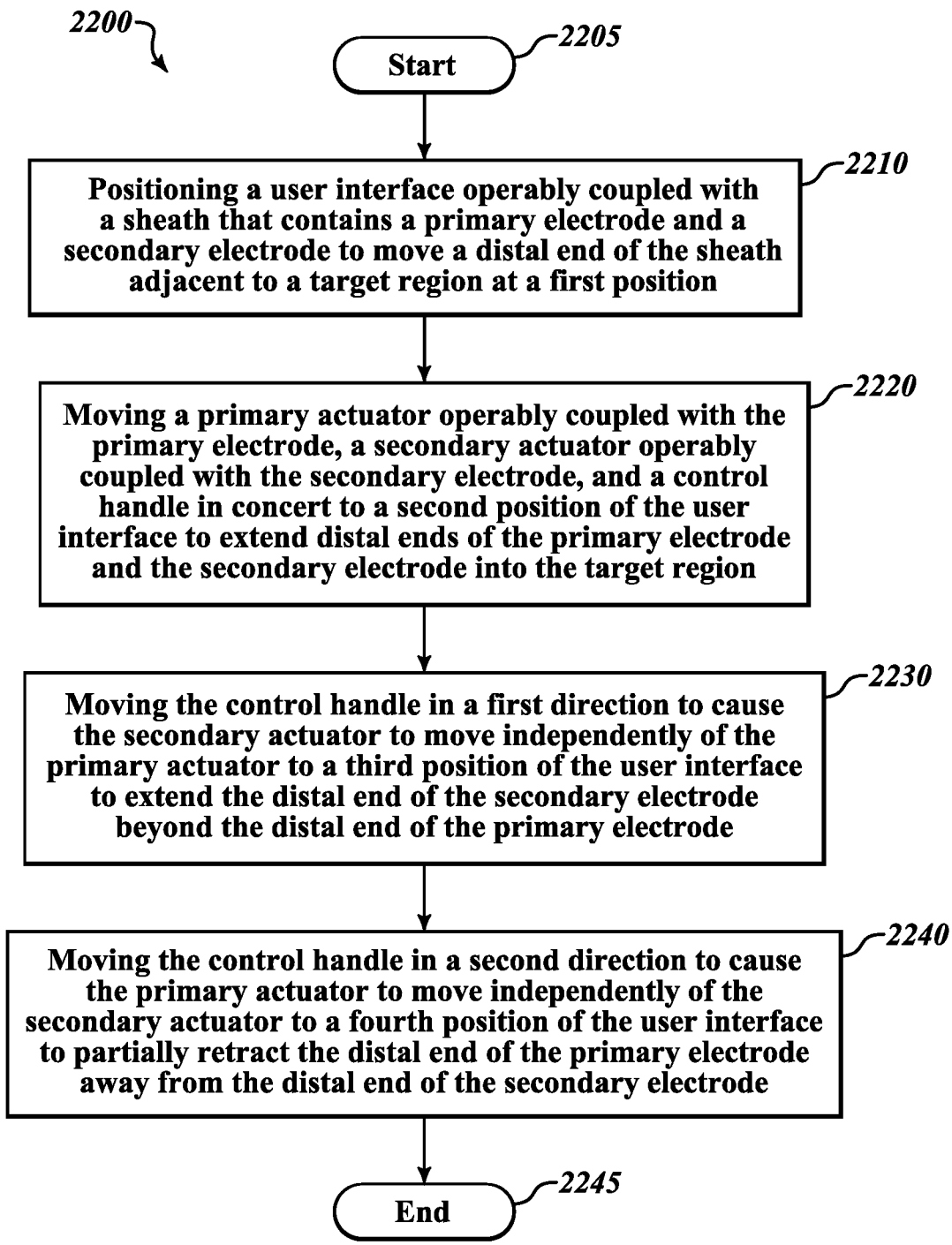

FIGS. 14A, 15A, 16A, 17A, 18A, 19A, 20A, and 21A are side views of an embodiment of a user interface for positioning multiple components relative to the reference point;

FIGS. 14B, 15B, 16B, 17B, 18B, 19B, 20B, and 21B are schematic diagrams of positioning of distal ends of a sheath, primary electrode, and secondary electrode relative to a reference point corresponding to positions of the components of the user interface of FIGS. 14A, 15A, 16A, 17A, 18A, 19A, 20A, and 21A, respectively; and FIG. 22 is a flow diagram of an illustrative method of positioning components using a user interface.

DETAILED DESCRIPTION

The following description is merely illustrative in nature and is not intended to limit the present disclosure, application, or uses. It will be noted that the first digit of three-digit reference numbers, the first two digits of four-digit reference numbers correspond to the first digit of one-digit figure numbers and the first two-digits of the figure numbers, respectively, in which the element first appears.

The following description explains, by way of illustration only and not of limitation, various embodiments of user interfaces to position electrodes for electrosurgical apparatuses, as well as systems including such user interfaces and methods of using the same. As will be described in detail below, electrosurgical techniques position first and second electrodes adjacent a reference point where electrical treatment, such as ablative treatment, is to be applied. For a specific example, the user interfaces and methods of their use may be used for ablating and/or coagulating tissue, removing lesions, and for performing other medical procedures within the lung.

It will be appreciated that various embodiments of user interfaces described herein may help to simplify the process of positioning the electrodes and holding the electrodes in place. As will be described below, various embodiments of the user interface accomplish the selective positioning and locking in place of the electrodes by engaging, sliding, and/or rotating components.

Figure 1:
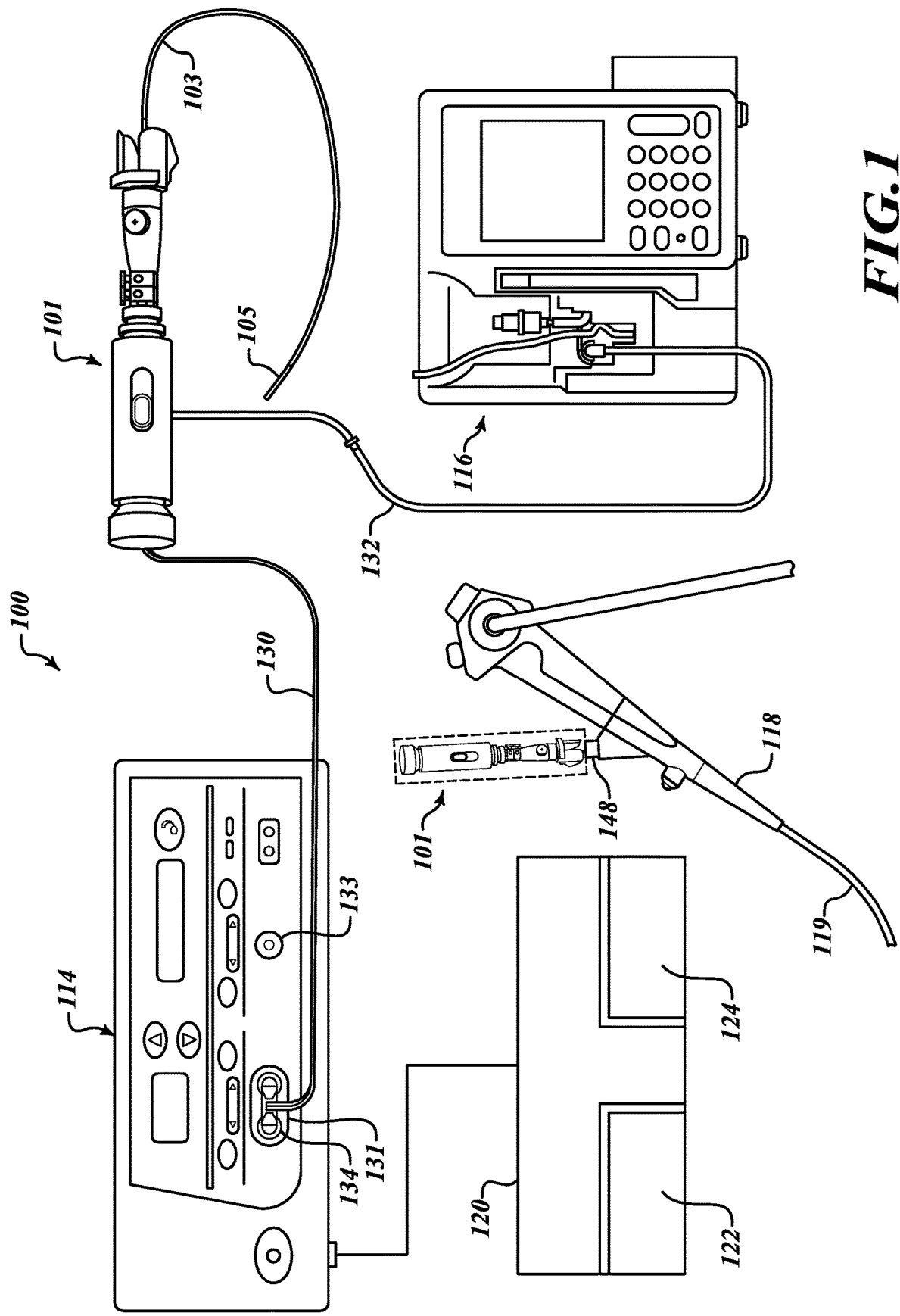
FIG. 1 is a block diagram in partial schematic form of an illustrative system for treating tissue.

Referring to FIG. 1, a system 100 is provided for treating tissue at a reference point in an anatomical region of a patient (not shown in FIG. 1). The system 100 may be a bipolar or monopolar radio frequency (RF) system, as desired, for treating tissue in a patient. Specifically, the system 100 may be employed for coagulation and/or ablation of soft tissue during percutaneous and/or endoscopic, including bronchoscopic, surgical procedures, such as, for example, partial and/or complete ablation of cancerous and/or noncancerous organ lesions. As will be further described, the tissue is treated by positioning one or more electrodes proximate the tissue to be treated and passing an electrical current through the tissue at a reference point.

In some embodiments, the system 100 includes a user interface 101, an electrosurgical radio frequency (RF) generator operating as a switchable current source 114, an infusion pump 116, and an electrosurgical instrument or apparatus, such as without limitation a bronchoscope 118. It will be appreciated that the electrosurgical instrument or apparatus may also include an endoscope or any other electrosurgical instrument as desired for a particular application. The bronchoscope 118 may be configured to receive the user interface 101 at a port 148 to enable the user interface 101 to manipulate electrodes at the reference point via the bronchoscope 118.

The user interface 101 electrically communicates with the switchable current source 114 though an electrical conductor 130. In some embodiments, the electrical conductor 130 is connected to an outlet 131 when the system is operated in a bipolar mode. The electrical conductor 130 may be coupled with the outlet 131 using an electrical connector 134 configured to electrically engage the outlet 131. In some other embodiments, the system 100 can be operated in a monopolar mode when the electrical conductor 130 is connected to a secondary outlet 133 with an adapter (not shown in FIG. 1) as desired. The user interface 101 is further connected to the infusion pump 116 with a tube 132 that facilitates the flow of liquid, for example saline solution, from the infusion pump 116 to the user interface 101.

The switchable current source 114 can be operated with the use of a foot operated unit 120 electrically connected to the switchable current source 114. The foot operated unit 120 includes a pedal 122 that instructs the switchable current source 114 to apply an electrical current to electrode(s) (described below) to cut and/or ablate tissue and a pedal 124 that instructs the generator 114 to apply a lower electrical current to the electrode(s) to coagulate tissue.

In various embodiments the bronchoscope 118 includes an insertion tube 119 that permits insertion of a sheath 103 into a body (not shown). A distal end 105 of the sheath 103 is delivered to a location near the tissue to be treated at the reference point. The sheath 103 contains and conveys the electrodes (not shown) to a desired treatment location. Positioning of the distal end 105 of the sheath 103 and the distal ends of the electrodes (not shown in FIG. 1) may be controlled by the user interface 101 received by the bronchoscope 118 at a port 148.

Referring to FIGS. 2-6, distal ends of components are positioned relative to a reference point 201 using various embodiments of a user interface. The reference point 201, for example, may be at a point within a target region 202 such as a lesion or any portion of tissue to be treated within a body. Given by way of illustration only and not of limitation, the illustrative embodiments of the user interface described below all are capable of positioning the components as described with reference to FIGS. 2-6, as further described with reference to each of the described embodiments. The description of FIGS. 2-6 is provided as a baseline to describe the operation of the various embodiments of the user interface.

In particular embodiments, a secondary electrode 211 is slidably received within a primary electrode 207, and the primary electrode 207 is slidably received within a sheath 203. In particular embodiments, until a user interface is manipulated to separately move the primary electrode 207 and/or the secondary electrode 211, the primary electrode 207 and the secondary electrode 211 move in concert with the sheath 203, which means that the electrodes 207 and 211 move at a same time and through a same distance as the sheath 203. As will be described below, in some instances, the secondary electrode 211 also may move in concert with the primary electrode 209 while both electrodes move independently of the sheath 103. Components contained within other components are represented with dashed lines in FIGS. 2-6.

Figure 2:
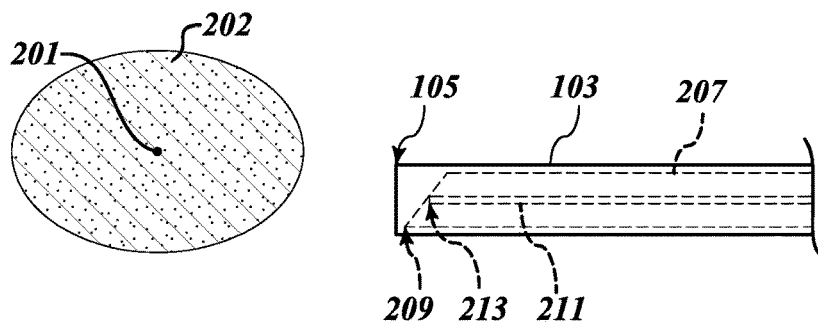
FIGS. 2-6 are schematic diagrams of positioning of distal ends of a sheath, primary electrode, and secondary electrode relative to a reference point.

Referring to FIG. 2, the sheath 203, the primary electrode 207, and the secondary electrode 211 are shown as they are positioned at an initial position relative to the reference point 201 at or near the target region 202. More particularly, FIG. 2 shows the components as they might be positioned upon the insertion of the sheath 203 through an insertion tube in a bronchoscope, such as the insertion tube 119 and the bronchoscope 118 of FIG. 1, before they are moved into precisely desired locations by manipulating the user interface (not shown) as further described below.

A distal end 205 of the sheath 203 is positioned close to the target region 202. The primary electrode 207 is slidably received within the sheath 203, with a distal end 209 of the primary electrode 207 at or near the distal end 205 of the sheath. Specifically, FIG. 2, for example, shows the distal end 209 of the primary electrode 207 positioned just short of the distal end 205 of the sheath 203. In turn, the secondary electrode 211 is slidably received within the primary electrode 207, with the distal end 213 of the secondary electrode 211 positioned just within the distal end 209 of the primary electrode 207.

Figure 3:
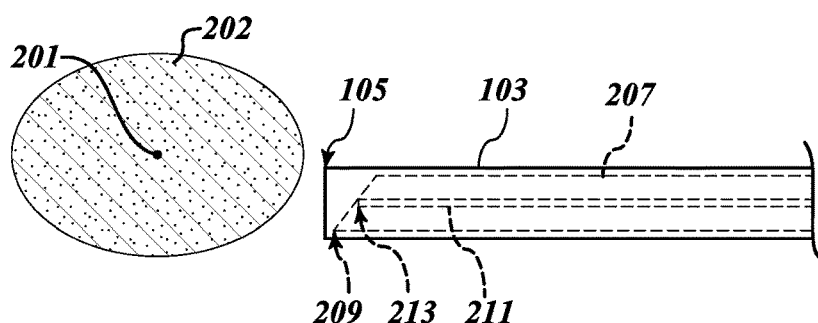

Referring to FIG. 3, the sheath 203, the primary electrode 207, and the secondary electrode 211 are shown as they are positioned once the sheath 203 has been moved closer to the target region 202. As contrasted with FIG. 2, in FIG. 3, a distal end 205 of the sheath 203 has been moved closer to the reference point 201 at the edge of the target region 202. Just as in FIG. 2, because the primary electrode 207 and the secondary electrode 211 have not been separately moved through the manipulation of a user interface (not shown), the primary electrode 207 and the secondary electrode 211 have moved with the movement of the sheath 203. Thus, at the deployment position closer to the reference point 201, the distal end 209 of the primary electrode 207 remains positioned just short of the distal end 205 of the sheath 203. Similarly, the distal end 213 of the secondary electrode 211 remains positioned just within the distal end 209 of the primary electrode 207. As will be further described with reference to embodiments of a sheath lock that may be part of a user interface or used in conjunction with a user interface, once the distal end 205 of the sheath 203 has been moved to a desired location, the sheath 203 may be locked in place.

Figure 4:
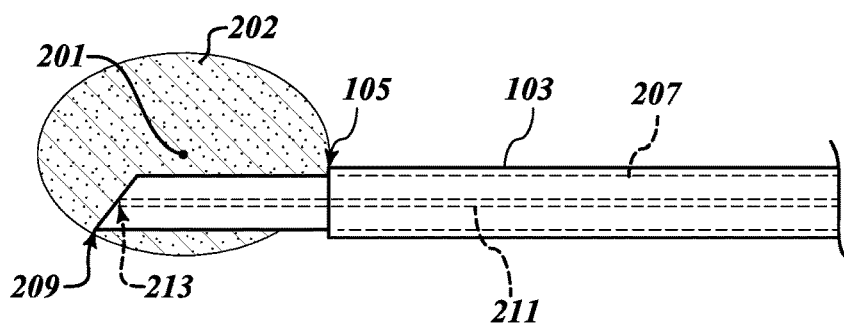

Referring to FIG. 4, the sheath 203, the primary electrode 207, and the secondary electrode 211 are shown as they are positioned once the primary electrode 207 has been extended from the sheath 203 toward the reference point 201 and into the target region 202. In particular embodiments, unless the user interface (not shown) is manipulated to disengage movement of the secondary electrode 211 from movement of the primary electrode 207, the secondary electrode 211 moves in concert with the primary electrode 207, with the secondary electrode 211 moving in the same direction and the same distance as the primary electrode 207. Thus, as shown in FIG. 4, the primary electrode 207 as the primary electrode 207 is extended beyond the distal end 105 of the sheath 103, and the secondary electrode 211 moves in concert with the primary electrode 207. As shown in FIG. 4, the distal end 209 of the primary electrode 207 is extended toward the reference point 201 and beyond the distal end 205 of the sheath 203. The distal end 213 of the secondary electrode 211 remains positioned just within the distal end 209 of the primary electrode 207. In particular embodiments, the primary electrode 207 is in the form of a needle, with the distal end 209 being configured to pierce tissue, such as tissue comprising the target region 202, to enable the distal end 209 of the primary electrode 207 to reach a desired position, and to be able to situate the secondary electrode 211 at a desired point.

As will be further described below, once the distal end 205 of the sheath 203 is in a desired location and locked in place, embodiments of the user interface allow the primary electrode 207 to be unlocked so that the primary electrode 207 may be moved independently of the sheath 103. As also further described below, embodiments of the user interface may keep motion of the secondary electrode 211 locked with motion of the primary electrode 207 so that the distal end 213 of the secondary electrode 211 moves in concert with the distal end 209 of the primary electrode 207. As also further described below, embodiments of a user interface permit one or both of the primary electrode 207 and the secondary electrode 211 to be fixed in position—that is, remain in place—so that one or both of the electrodes 207 and 211 are secured at a current position. Thus, for example, a position of the primary electrode 207 may be fixed while the secondary electrode 211 may be moved independently of the primary electrode 207, or a position of the secondary electrode 211 may be fixed while the primary electrode 207 may be moved independently of the secondary electrode 211. Also, both electrodes 207 and 211 may be fixed in place, for example, when treatment is administered by applying an electrical current using an electrosurgical apparatus such as that shown in the system 100 of FIG. 1.

Figure 5:
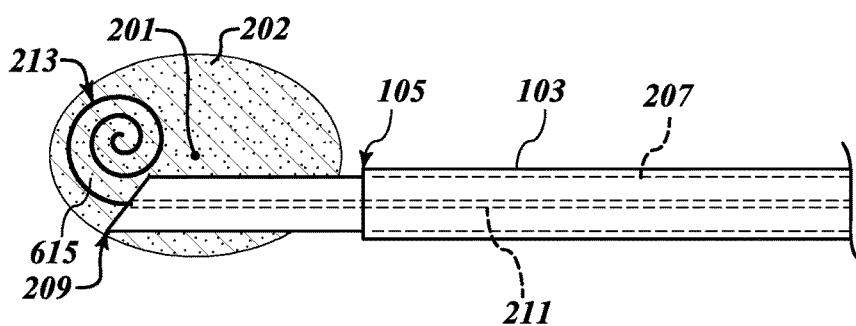

Referring to FIG. 5, the sheath 203, the primary electrode 207, and the secondary electrode 211 are shown as they are positioned once the secondary electrode 211 has been extended from the primary electrode 207. A distal end 213 of the secondary electrode 211 is deployed at a position on an opposite side of the reference point 201 and at an opposite side of the target region 202 from the primary electrode 207. In particular embodiments, the secondary electrode 211 is configured as coiled wire which is received within the primary electrode 207 in a straightened form. Once the user interface is manipulated to independently extend the secondary electrode 211 from the primary electrode 207, the secondary electrode 211 coils. As a result, the distal end 213 of the secondary electrode 211 corkscrews into tissue at the target region 202. The corkscrewing of the distal end 213 of the secondary electrode 211 may assist in securing the position of the distal end 213 of the secondary electrode 211 during treatment. FIG. 5 also shows insulation 215 along a length of the secondary electrode 211, but which stops short of the distal end 213 of the secondary electrode 211. The insulation 215 electrically insulates the secondary electrode 211 from the primary electrode 207 such that, when electrical current is applied to proximal ends (not shown) of the primary electrode 207 and the secondary electrode 211, the electrical current may only flow between the distal end 209 of the primary electrode 207 and the uninsulated distal end 213 of the secondary electrode 211.

Figure 6:
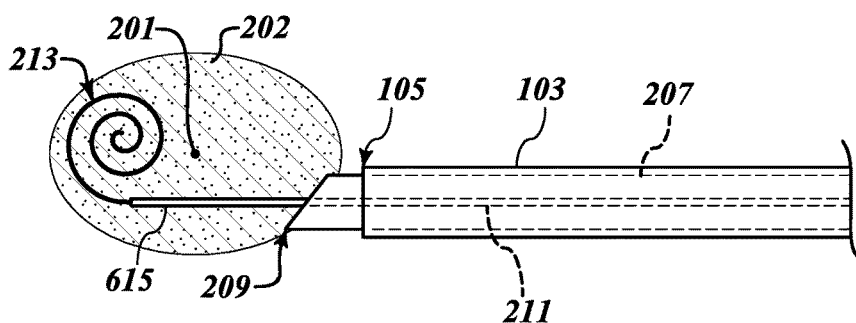

Referring to FIG. 6, the sheath 303, the primary electrode 207, and the secondary electrode 511 are shown as they are positioned once the primary electrode 207 is partially retracted away from the reference point 201 and partially retracted from the target region 202 and into the sheath 503. As previously described, a needle shape of the primary electrode 207 assists in positioning the distal end 213 of the secondary electrode 211 at a desired location. Once the distal end 213 of the secondary electrode 211 has been disposed at that location, however, it may be desired to move a distal end 209 of the primary electrode 207 away from the reference point 201 to create a desirable gap between the distal end 213 of the secondary electrode 211 and the distal end 209 of the primary electrode 207 across which electrical current may be applied to treat tissue at the target region 202 near the reference point 201.

Except for a portion of the secondary electrode 211 toward the distal end 213 of the secondary electrode 211 may be coated with an insulation 615 to electrically isolate the secondary electrode 211 from the primary electrode 207. Partial retraction of the primary electrode 207 thus creates a gap between the electrically exposed distal end 209 of the primary electrode 207 and the electrically exposed distal end 213 of the secondary electrode 211, permitting ablation or other operations as a result of applying current across the resulting gap. As will be described further below, once the distal end 213 of the secondary electrode 211 has been secured at a desirable location, embodiments of the user interface (not shown in FIG. 6) permit the primary electrode 207 to be unlocked and moved independently from the secondary electrode 211 to enable the partial retraction shown in FIG. 6. Once partially retracted, embodiments of the user interface also enable the primary electrode 207 to be locked in place.

Referring to FIGS. 7A and 7B, an apparatus 700 includes an illustrative user interface 701 received at a port 748 of an electrosurgical apparatus 718, such as a bronchoscope or another minimally invasive device used for performing diagnostic or therapeutic tasks by extending a sheath or catheter into a body (not shown in FIGS. 7A and 7B). In the apparatus 700 of FIG. 7A, the user interface 701 includes a sheath actuator 704 and a sheath lock 706 configured to move the sheath 103 to a desired location to position a distal end 105 of the sheath 103 relative to the reference point 201. In some embodiments, the sheath actuator 704 may be a slidable mechanism incorporating a slidable sleeve 712 that is received within a collar 714. The slidable sleeve 712 may be locked in position at the collar 714 by the sheath lock 706. The sheath lock 706 may be a spring-loaded locking pin, a thumbscrew, or another mechanism configured to mechanically engage the slidable sleeve 712 to secure the slidable sleeve 712—and, in turn, the sheath 703—in place at a desired location.

In some embodiments, the sheath actuator 704 may be part of the user interface 701. For example, in the user interface 701 of FIG. 7A the slidable sleeve 712 is fixably engaged with an interface housing 710 at a distal end 716 of the interface housing 710. The collar 714 then may engage the port 748 on the electrosurgical apparatus 718, where movement of the slidable sleeve 712 within the collar 714 controls movement of the sheath 103. In some other embodiments, the sheath actuator 704 may, for example, be part of the electrosurgical apparatus 718. The collar 714 may be fixably joined to the port 748. The slidable sleeve 712 may be associated with the port 748 to engage the distal end 716 of the interface housing 710. In another embodiment, the slidable sleeve 712 may be fixably joined to the distal end 716 of the interface housing 710 and be configured to receivably engage the collar 714 that is fixably attached to the port 748. Any of these embodiments of the sheath actuator 704 may facilitate movement of the sheath 103 as described below.

In various embodiments the user interface 701 is mechanically coupled with a primary electrode 207 slidably received within the sheath 103, with a distal end 209 of the primary electrode 207 positioned just short of the distal end 105 of the sheath 103. The user interface 701 is also mechanically coupled with a secondary electrode 211 slidably received within the primary electrode 207, with the distal end 213 of the secondary electrode 211 positioned just within the distal end 209 of the primary electrode 207. Embodiments of the user interface 701 may be configured to secure the primary electrode 207 and the secondary electrode 211 relative to the sheath 103 so that both the primary electrode 207 and the secondary electrode 211 move in concert with the sheath 103 as the sheath is moved as described with reference to FIG. 3.

Referring to FIGS. 8A and 8B, manipulation of the sheath actuator 704 illustrates an example of how the sheath 103 may be unlocked and moved into position as previously described with reference to FIG. 3. In the configuration shown in FIGS. 8A and 8B, the sheath actuator 704 has been manipulated to enable the sheath 103 to be moved a distance 819 closer to the reference point 201 and the target region 202. Specifically, once the sheath lock 706 of the sheath actuator 704 is manipulated to enable movement of the slidable sleeve 712 within the collar 714, the interface housing 710 is moved the distance 819 to move the sheath 103 the same distance 819 toward the reference point 702. Once the sheath 103 has reached the desired location, the slidable sleeve 712 may be locked in position at the collar 714 by the sheath lock 706. As will be described further below, embodiments of the user interface 701 maintain the positions of the primary electrode 207 and the secondary electrode 211 relative to the sheath 103 as the sheath actuator 704 is used to move the sheath 103. Therefore, a distal end 209 of the primary electrode 207 and a distal end 213 of the secondary electrode 211 also are moved by the distance 219 toward the reference point 201.

Figure 9:
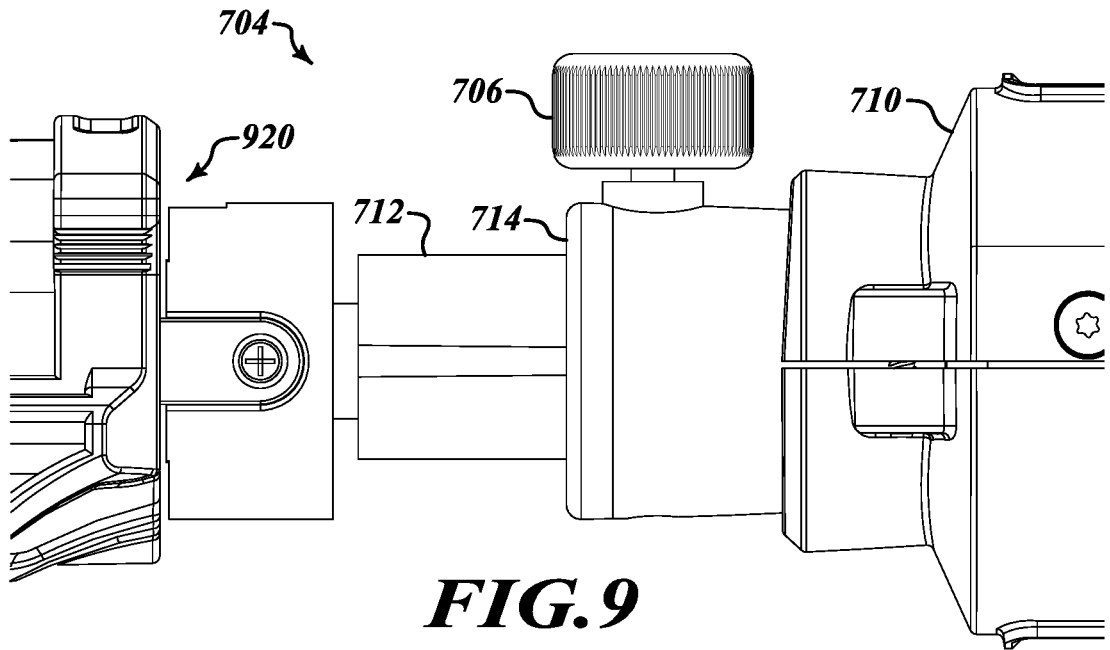
FIG. 9 is a side view of an illustrative sheath actuator and a sheath lock.

Referring to FIG. 9, an enlarged external view shows an illustrative sheath actuator 704 and a sheath lock 706 in greater detail. The sheath actuator 704 includes a slidable sleeve 712 that is fixably attached to a coupling 920 configured to engage a port (not shown in FIG. 9) of an electrosurgical apparatus (not shown in FIG. 9) such as a bronchoscope. The sheath lock 706 in the embodiment of FIG. 9 is a thumbscrew that may be loosened to permit movement of a collar 714 fixably attached to the interface housing 710 to move the sheath (not shown in FIG. 9) as previously described with reference to FIGS. 7 and 8. After the interface housing 710 has been manipulated to slide the collar 714 relative to the slidable sleeve 712 to move the sheath to a desired location, the sheath lock 706 is reengaged, such as by turning a thumbscrew, to fix the position of the sheath.

Figure 10:
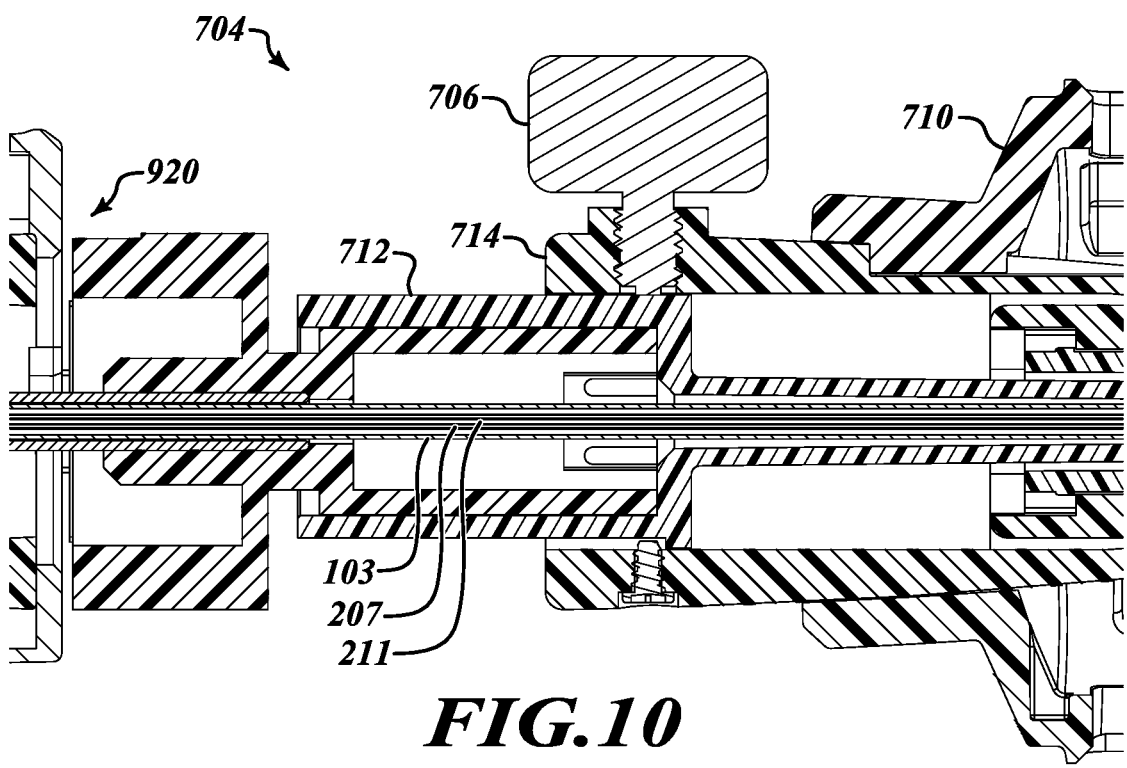
FIG. 10 is a cutaway view of the sheath actuator and sheath lock of FIG. 9.

Referring to FIG. 10, a cutaway view of the illustrative sheath actuator 704 shows internal operation of the sheath actuator 704 of FIG. 9. As previously described, the sheath actuator 704 includes the slidable sleeve 712 that is fixably attached to the coupling 920. In some embodiments the sheath lock 706 is a thumbscrew that may be loosened to permit movement of the collar 714 fixably attached to the interface housing 710 to move the sheath 103 and, in concert therewith, the primary electrode 207 and the secondary electrode 211 received within the sheath 103. After the interface housing 710 is manipulated to slide the collar 714 relative to the slidable sleeve 712 to move the sheath 103 to the desired location, the sheath lock 706 is turned to fix the position of the collar 714 relative to the slidable sleeve 712 to fix the position of the sheath 103.

Figure 11:
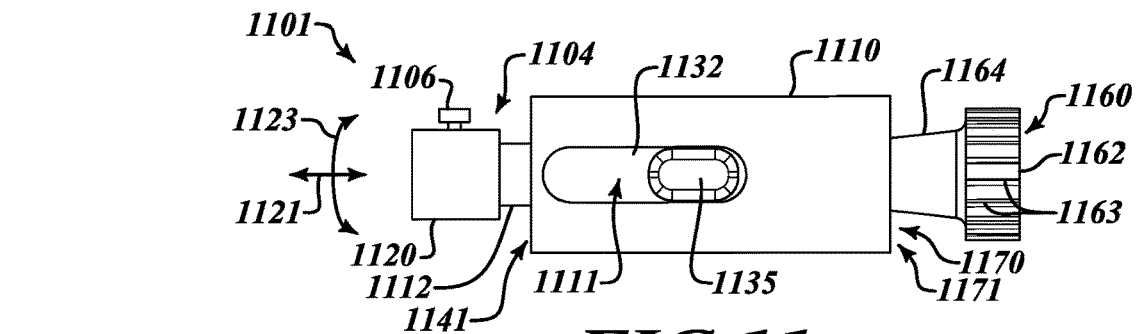
FIG. 11 is a side view of an embodiment of a user interface for positioning multiple components relative to the reference point.

Referring to FIG. 11, in various embodiments an illustrative user interface 1101 for positioning electrodes includes a housing 1110 that supports components that are moved parallel along an axis 1121 or rotated along a curve 1123 around the axis 1121, as further described below. As also further described below, the user interface 1101 generally is controlled by moving actuators, such as the primary actuator 1132, by engaging a primary actuator button 1135 through a first access opening 1111 defined in the housing 1110. The primary actuator 1132 may be moved along the axis 1121 by engaging and manipulating the primary actuator button 1135 to slide the primary actuator 1132 along the axis 1121 toward a first end 1141 of the housing 1110. As described below, initially, a secondary actuator 1252 (FIG. 12) and a control handle 1160 are configured to initially move in concert with the primary actuator 1132. Although not shown in FIG. 11, the primary actuator 1132 may slide along a shaft that may be coupled with the housing 8210 at the first end 1141 of the housing 1110. The shaft may be hollow to receive and permit sliding of electrodes (not shown in FIG. 11) therethrough.

The user interface 1101 includes a coupling 1120 to engage a port on an electrosurgical apparatus, such as a bronchoscope, as described with reference to FIGS. 1, 7, and 8. The user interface 1101 also includes a sheath actuator 1104 to position a sheath (not shown in FIG. 11) as previously described with reference to FIGS. 7-11. The sheath actuator 1104 includes a slidable sleeve 1112 and a sheath lock 1106 to secure the slidable sleeve 1112 in place at the first end 1141 of the housing 1110 of the user interface 1101, as described further below. It will be appreciated that a sheath actuator may be part of the bronchoscope or a separate device inserted between and coupled with the user interface 1101 and the bronchoscope (not shown in FIG. 11). Thus, the sheath actuator 1104 may not be a part of the user interface 1101. Also, although not shown in FIG. 11, leads from a switchable current source are received at the user interface 1101 and a sheath containing primary and secondary electrodes extends from the user interface 1101 via the coupling 1120.

An actuator opening 1170 at a second end 1171 of the housing 1110 receives the control handle 1160. The control handle 1160 includes a control knob 1162 which may include a number of raised protrusions 1163 to facilitate a user's gripping and rotating of the control knob 1162, as further described below with reference to FIGS. 12, 16A, and 19A. The control handle 1160 also includes a tapered body 1164 that engages the primary actuator 1132 to cause the primary actuator 1132 to engage the housing 1110, as further described below.

Figure 12:
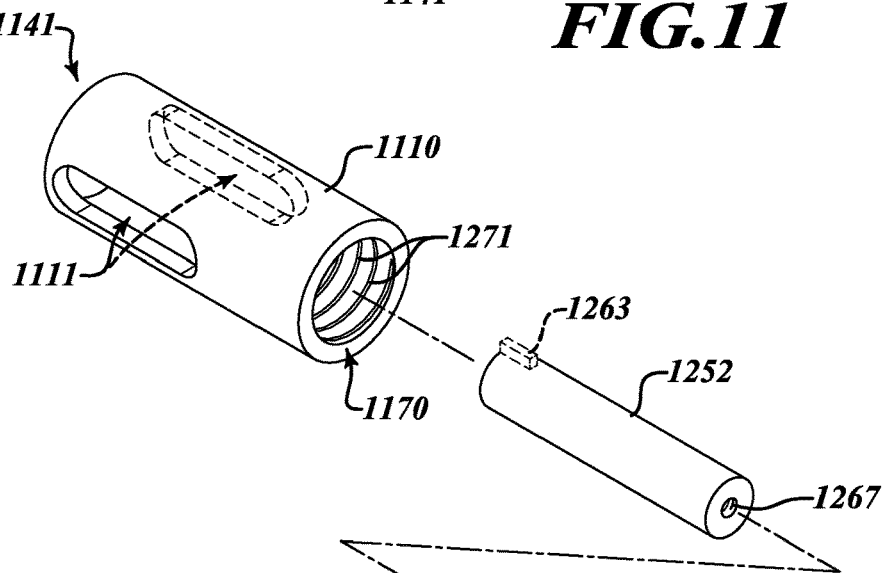
FIG. 12 is a perspective, exploded view of the user interface of FIG. 11.

Referring to FIG. 12, the user interface 1101 includes a number of components, including the housing 1110, the primary actuator 1132, a secondary actuator 1252, and components of the sheath actuator 1104, including the slidable sleeve 1112, the sheath lock 1106, and the coupling 1120. As previously described, the first access opening 1111 defined in the housing 1110 permits access to the primary actuator button 1135 and, thus, to the primary actuator 1132. The housing 1110 also includes the actuator opening 1170 that receives the control handle 1160. The actuator opening 1170 includes receptive threads 1271 to engage insertive threads 1260 projecting from the primary actuator 1132 to control movement of the primary electrode, as further described below.

The primary actuator 1132, which may be manipulated by a user engaging the primary actuator button 1135 may slidably and rotatably move within the housing 1110. The primary actuator 1132 is operably engaged with a primary electrode (not shown in FIG. 12) so that movement of the primary actuator 1132 relative to the axis 1121 (FIG. 11) also moves the primary electrode. The housing 1110 may include access openings 1111 on opposing sides of the housing 1110 to enable a user to access the primary actuator button 1135 to manipulate the primary actuator 1132. Although not shown in the figures, the primary actuator 1132 may support an additional grip, on a side opposite the primary actuator 1132 from the primary actuator grip 1135, to facilitate user manipulation of the primary actuator 1132. As described further below, the primary actuator 1132 may be moved by manipulating the primary actuator button 1135 or by moving the control handle 1160.

As previously described, the housing 1110 may include access openings 1111 on opposing sides of the housing 1110 to enable a user to access the primary actuator button 1135 to manipulate the primary actuator 1132. In various embodiments, to facilitate concerted movement of the primary actuator 1132 and the secondary actuator 1252, the primary actuator button 1135 may be configured to move laterally to the axis 1121 (FIG. 11) so that pressing the primary actuator button 1135 frictionally or otherwise mechanically engages the secondary actuator 1252. As a result, pressing the primary actuator button 1135 while sliding the primary actuator 1132 along the axis 1121 enables the primary actuator 1132 and the secondary actuator 1252 to move in concert. Releasing the primary actuator button 1135 releases the primary actuator 1132 from the secondary actuator 1252 to permit independent movement of the primary actuator 1132 and the secondary actuator 1252.

In various embodiments, the primary actuator 1132 includes a spreadable body portion 1230 supporting a plurality of insertive threads 1260 on opposing sides 1236 of the primary actuator 1132 to selectively engage the receptive threads 1271 within the actuator opening 1170 of the housing 1110. When it is desired to move the primary electrode independently of the secondary electrode, as further described below, the tapered body 1164 of the control handle 1160 is inserted into the primary actuator 1132 causing the sides 1236 of the spreadable body portion 1230 to spread apart. The spreading of the spreadable body portion 1230 moves the insertive threads 1260 on the primary actuator 1132 outwardly to engage the receptive threads 1170 within the housing 1110.

In various embodiments, the primary actuator 1132 includes tabs 1234 configured to engage corresponding slots 1265 defined by the control handle 1160. The slots 1265 on the control handle 1160 laterally engage the tabs 1234 on the primary actuator 1232. As a result, with the engagement of the insertive threads 1260 extending from the primary actuator 1132 with the receptive threads 1271 of the housing 1110, turning the control handle 1160 causes the primary actuator 1132 to rotate and translate relative to the housing 1110, thereby moving the primary electrode as further described below with reference to FIGS. 17A-18B.

The secondary actuator 1252 is movably received within the primary actuator 1132, enabling the primary actuator 1132 to slide and/or rotate independently of the secondary actuator 1152. The secondary actuator 1252 is operably engaged with a secondary electrode (not shown in FIG. 12) so that any movement of the secondary actuator 1252 relative to the axis 1121 (FIG. 11) also moves the secondary electrode. In various embodiments, the secondary actuator may include a guide tab 1263 or similar mechanism that engages a corresponding structure (not shown) of the housing 1110. The guide tab 1263 is configured to prevent the secondary actuator 1252 and the connected secondary electrode (not shown in FIG. 12) from rotating when the primary actuator 1132 is rotated relative to the secondary actuator 1252, as described further below with reference to FIGS. 17A-18B.

The secondary actuator 1252 may engage the control handle 1160 via a disengageable linkage. In various embodiments, the disengageable linkage may include an orifice 1265 including receptive threads 1267 configured to receive an insertive member 1270 with corresponding insertive threads 1275 extending from the control handle 1160. In various embodiments, the insertive member 1270 and the orifice 1265 may be sized so that the insertive member 1270 at least partially remains within the orifice 1265 throughout operation, although rotation of the control handle 1160 relative to the secondary actuator 1152 permits lateral movement of the control handle 1160 relative to the secondary actuator along the axis 1121 (FIG. 11). In various embodiments, a pitch of the receptive threads 1267 and the insertive threads 1275 is the same as that of the insertive threads 1260 of the primary actuator 1132 and the receptive threads 1271 of the housing 1110 so that rotation of the control handle 1160 results in movement of the primary actuator 1132 along the axis 1121 that corresponds with the displacement of the control handle 1160 from the secondary actuator 1152, leaving the secondary actuator 1152 in place as the primary actuator 1132 is moved, as described below with reference to FIGS. 17A and 17B.

In an initial configuration, the orifice 1265 of the secondary actuator 1252 is threadably coupled with the insertive member 1270 of the control knob 1160 so that sliding of the control knob 1160 along the axis 1121 (FIG. 11) causes the secondary actuator 1252 to slide, resulting in a corresponding movement of the associated secondary electrode (not shown in FIG. 12). As further described below with reference to FIGS. 16A-17B, at this point, the tapered body 1164 of the control handle 1160 spreads the spreadable body portion 1230 of the primary actuator 1132 to expand to cause the insertive threads 1260 of the primary actuator 1132 to engage the receptive threads 1271 of the housing 1110. Then, by rotating the control knob 1160, the control knob 1160 may cause the primary actuator 1132 to rotate and to translate along the axis 1121 as a result of the engagement of the insertive threads 1260 of the primary actuator 1132 with the receptive threads 1271 of the housing 1110. At the same time, the rotation of the control knob 1160 causes the insertive member 1270 of the control knob 1160 to threadably disengage from the orifice 1265 the secondary actuator 1252. With the insertive threads 1260 of the primary actuator 1132, the receptive threads 1160 of the housing 1110, the receptive threads 1267 of the orifice 1265, and the insertive threads 1275 of the insertive member 1270 all having an equal pitch, rotation of the control handle 1160 results movement of the primary actuator 1132 that is equal to the displacement of the control handle 1160 from the secondary actuator 1252. Thus, the rotation of the control knob 1160 moves the primary actuator 1132 while leaving the secondary actuator 1152 in place, as further described below with reference to FIGS. 17A-18B.

Figure 13:
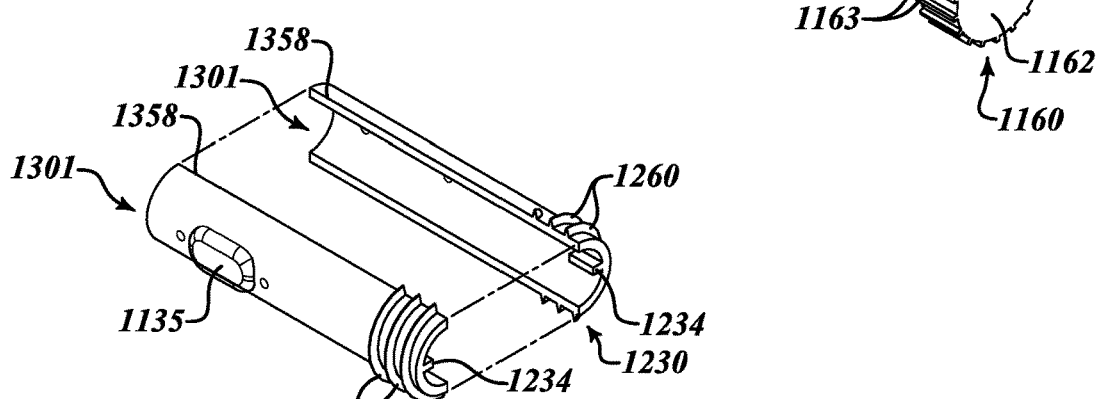
FIG. 13 is a perspective, exploded view of an embodiment of a secondary actuator as used in the user interface of FIG. 11.

Referring to FIG. 13, in various embodiments the primary actuator 1132 may include two sections 1358 to facilitate expansion of the spreadable body portion 1230 of the primary actuator 1132. In various embodiments, each of the two sections 1358 includes a half of the insertive threads 1260 for engaging the receptive threads 1271 in the housing 1110 and a tab 1234 for engaging one of the slots 1265 on the control handle 1160. The sections 1358 may be mechanically or adhesively joined at a first end 1301 of the primary actuator 1132 to partially hold the two sections 1358 of the primary actuator 1132 together while enabling the spreadable body portion 1230 of the primary actuator 1132 that supports the insertive threads 1260 to spread apart. Thus, the sections 1358 are held together at one end while enabling the spreadable body portion 1230 of the primary actuator 1132 to spread apart so that the insertive threads 1260 on the primary actuator 1132 may engage the receptive threads 1271 of the housing 1110. In various other embodiments (not shown), the primary actuator 1132 also may be formed as a single component with a cut being formed on a line between the two tabs 1234 to form the spreadable body portion 1230 of the primary actuator 1132.

Referring to FIGS. 14A-21B, manipulating of the user interface 1101 and corresponding movements of the sheath 103, the primary electrode 207, and the secondary electrode 211 are described.

Figure 14A:
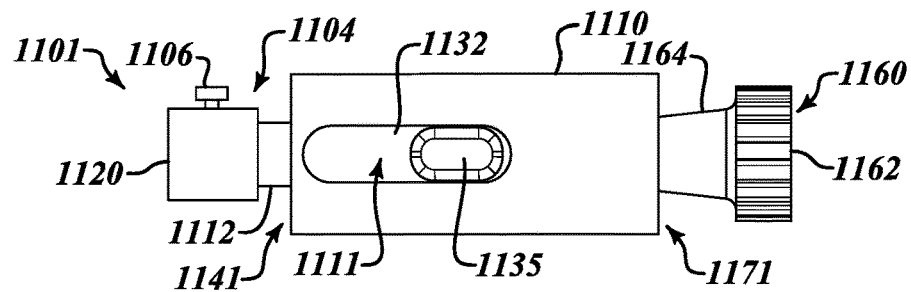
Figure 14B:
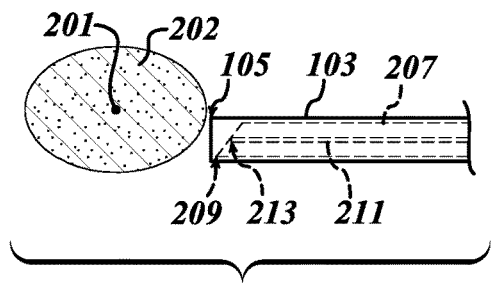

Referring to FIGS. 14A and 14B, the sheath actuator 1104 is used to position the sheath 103 to place electrodes 207 and 211 adjacent the target region 202 about a reference point 201. As previously described with reference to FIGS. 3 and 7A-10, the sheath actuator 1104 controls a position of the sheath 103. Specifically, a position of the sheath 103 is controlled by sliding the slidable sleeve 1112 within the coupling 1120 and securing the sheath 103 at the desired location by securing the slidable sleeve 1112 with the sheath lock 1106. The sheath actuator 1104 may operate similarly to the sheath lock 706 of FIG. 9, as previously described. In various embodiments, the slidable sleeve 1112 is fixably mounted to the housing 1110 and is slidably received within the coupling 1120. When the slidable sleeve 1112 is situated to position the sheath 103 that contains the electrodes 207 and 211 at a desired location, the sheath lock 1106 is locked to secure the slidable sleeve 1112 in place. The sheath lock 1106 may be a spring-loaded lock, a thumbscrew, or another similar mechanism as previously described with reference to FIGS. 7A-10 to secure the slidable sleeve 1112 in place to secure the position of the sheath 103.

As previously described and as shown in the FIG. 14B, in illustrative embodiments the secondary electrode 211 is received within the primary electrode, with a distal end 213 of the secondary electrode 211 initially resting just within the distal end 209 of the primary electrode 207. In turn, the distal end 209 of the primary electrode 207 rests just within the distal end 105 of the sheath 103. The sheath actuator 8204 is used to position the distal end 105 of the sheath 103 adjacent the target region 202 near the reference point 201 as previously described with reference to FIGS. 3 and 7A-10.

Figure 15A:
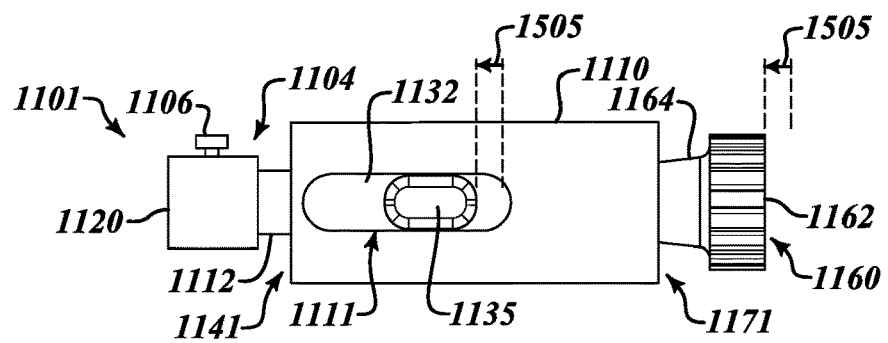
Figure 15B:
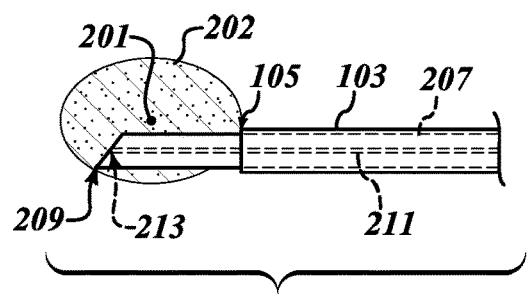

Referring to FIGS. 15A and 15B, once the distal end 105 of the sheath 103 is positioned adjacent the target region 202, the user interface 1101 may be used to move the electrodes 207 and 211 to desired positions. Referring to FIG. 15A, the primary actuator 1132 is advanced toward the first end 1141 of the housing 1110, such as by a user engaging the primary actuator button 1135 and sliding the primary actuator 1132 a distance 1505 toward the first end 1141 of the housing 1110. As previously described with reference to FIG. 12, in various embodiments, depressing the primary actuator button 1135 frictionally or otherwise mechanically engages the primary actuator 1132 with and the secondary actuator 1152. As a result, moving the primary actuator 1132 causes the secondary actuator 152 to move in concert with the primary actuator 1132. Also, in an initial configuration, the insertive member 1270 of the control handle is threadably engaged with the orifice 1265 of the secondary actuator 1252, as previously described with reference to FIG. 12. Thus, engaging the primary actuator button 1135 and moving the primary actuator 1132 causes the secondary actuator 1152 and the control handle 1160 to all move in concert by the distance 1505 as shown in FIG. 15A. Once the electrodes are positioned as desired, the user may release the primary actuator button 1135.

Referring to FIG. 15B, the movement of the primary actuator 1132 and the concerted movement of the secondary actuator 1252 shown in FIG. 15A results in the primary electrode 207 and the secondary electrode 211 moving through a same distance. As a result, the distal ends 209 and 213 of the electrodes 207 and 211, respectively, are moved in concert beyond the distal end 105 of the sheath 103. In the example of FIG. 15B, when the target region 202 includes an area of tissue and the primary electrode 207 is in the form of a needle, the primary electrode 207 and the secondary electrode 211 contained therein pierce the target region 202 near the reference point 201.

Figure 16A:
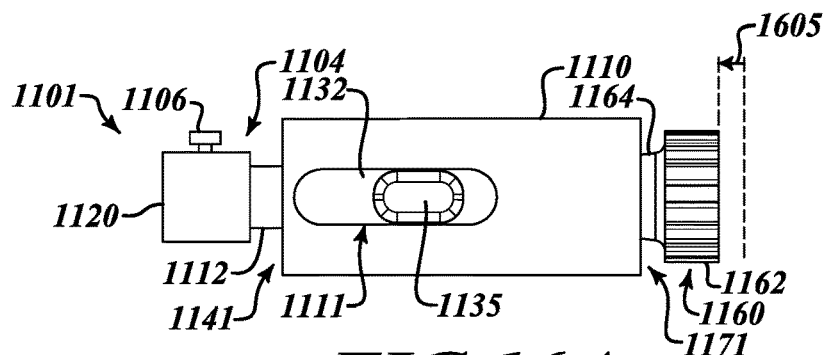
Figure 16B:
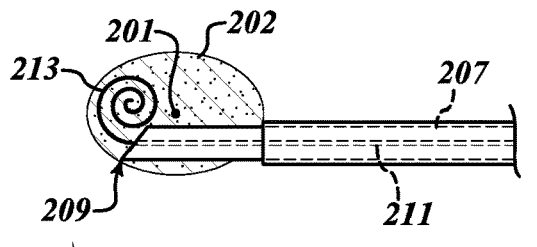

Referring to FIGS. 16A and 16B, once the distal ends 209 and 213 of the electrodes 207 and 211, respectively, are inserted into the target region 202, the user interface 1101 may be used to extend the secondary electrode 211 to a desired position. Referring to FIG. 16A, a user pushes the control handle 1160 through a distance 1605. As previously described, once the primary actuator button 1135 has been released, the secondary actuator 1252 may move independently of the primary actuator 1132. Thus, pushing the control handle 1160 through the distance 1605 moves the secondary actuator 1152 without moving the primary actuator 1132.

Referring to FIG. 16B, the movement of the control handle 1160 and the secondary actuator 1252 results in the distal end 213 of the secondary electrode 211 being extended into the target region 202 beyond the distal end 209 of the primary electrode 207. In various embodiments, once extended beyond the distal end 209 of the primary electrode 207, the secondary electrode 211 curls to auger into tissue or other material in the target region 202 to secure the secondary electrode 211 in place. With both electrodes 207 and 211 deployed, operations using the electrodes 207 and 211, such as treatment of tissue at the target region 202, may commence. Alternatively, as described below, further manipulation of the electrodes 207 and 211 may be conducted before commencing operation of the electrodes 207 and 211.

As previously described with reference to FIG. 12, the pushing of the control handle 1160 as shown in FIG. 15A also causes the tapered body portion 1164 of the control handle 1160 to cause the expansion of the spreadable body portion 1230 of the primary actuator 1132. This expansion causes the insertive threads 1260 of the primary actuator 1132 to engage the receptive threads 1270 on the housing 1110 to facilitate partial retraction of the primary electrode 207 by rotating the control handle 1160, as described with reference to FIGS. 17A and 17B.

Figure 17A:
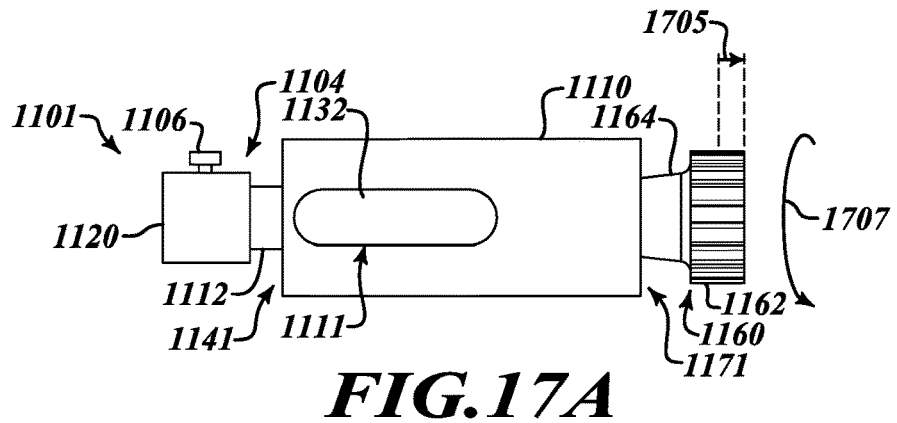
Figure 17B:
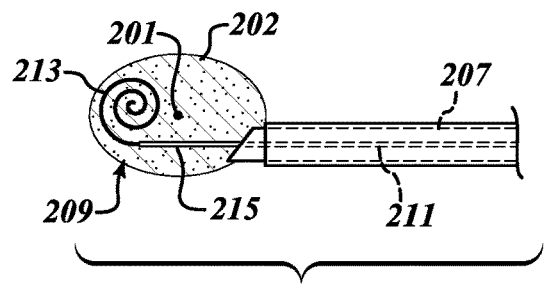

Referring to FIGS. 17A and 17B, it may be desired to partially retract the distal end 209 of the primary electrode 207 from the target region 202. Partially retracting the distal end 209 of the primary electrode 207 from the distal end 213 of the secondary electrode 211 opens a gap between them through which electrical current provided by the switchable current source 114 (FIG. 1) may be used to ablate or otherwise treat tissue in the target region 202. With the insertive threads 1260 of the primary actuator 1132 engaging the receptive threads 1270 on the housing 1110, rotation of the control handle 1160 through a rotational distance 1707 results in rotation of the primary actuator 1132 and in a translation of both the control handle 1160 and the primary actuator 1132 through a distance 1705. (Rotation of the primary actuator 1132 causes the primary actuator button 1135 to rotate out of the access opening 1111 of the housing 1110.) At the same time, the rotation of the control handle 1160 causes the control handle 1160 to threadably disengage from the secondary actuator 1252, as described in detail with reference to FIG. 12. Thus, rotation of the control handle 1160 results in movement of only the primary actuator 1132 and the primary electrode 207 while leaving the secondary actuator 1252 and the secondary electrode 211 in place.

Referring to FIG. 17B, the movement of the control handle 1160 and the primary actuator 1132 partially retracts the distal end 209 of the primary electrode 207 from the target region 202. As previously mentioned, the curling of the distal end 213 of the secondary electrode 211 desirably may help the distal end 213 of the secondary electrode 211 to hold its position as the distal end 209 of the primary electrode 207 is partially retracted. As shown in FIG. 17B, partial retraction of the primary electrode 207 exposes the insulated portion 615 of the secondary electrode 211, thereby creating electrical separation between the electrically exposed distal end 213 of the secondary electrode 211 and the electrically exposed distal end 209 of the primary electrode 207, as previously described with reference to FIG. 6. The gap between the electrically exposed distal ends 209 and 213 may be desirable in allowing ablation of electrically conductive tissues or other operations to be performed by applying electrical current across the resulting gap.

It will be appreciated that the extension of the distal end 213 of the secondary electrode 211 and the subsequent partial retraction of the distal end 209 of the primary electrode 207 are achieved by a user manipulating the control handle 1160 without engaging other portions of the user interface 1101. In other words, the user is able to separately manipulate the primary electrode 207 and the secondary electrode 211 using only the control handle 1160 which serves as a dual-action control surface.

After treatment or other operations permitted by the positioning of the electrodes 207 and 211 have been performed, operations of the user interface 1101 may be reversed in order to withdraw the distal ends 209 and 213 of the electrodes 207 and 211, respectively.

Figure 18A:
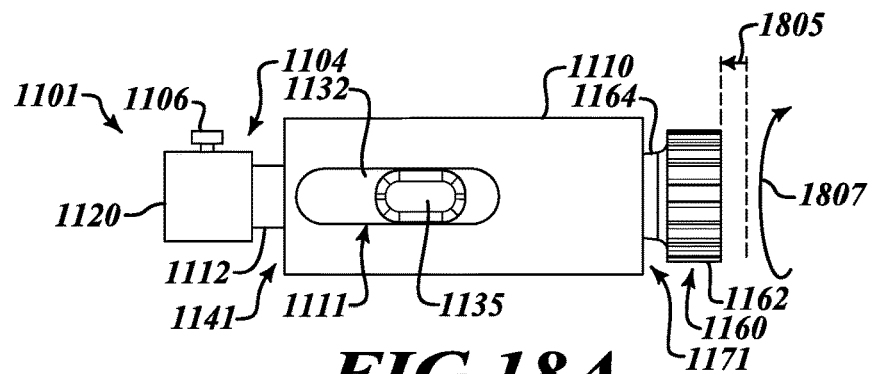

Referring to FIG. 18A, the distal end 209 of the primary electrode 207 is re-extended toward the distal end 213 of the secondary electrode by rotating the control handle 1160 through a rotational distance 1807. The rotational distance 1807 is an opposite of the direction and magnitude of the rotational distance 1707 (FIG. 17A) through which the control handle 1160 was rotated to partially retract the distal end 209 of the primary electrode 207. The insertive threads 1260 of the primary actuator 1132 remain engaged with the receptive threads 1271 of the housing 1110. Thus, the rotation of the control handle 1160 through the rotational distance 1807 causes the primary actuator 1132 to translate a distance 1805, which is opposite in direction and of the same magnitude of the distance 1705 through which the primary actuator translated 1132 in partially retracting the distal end 209 of the primary electrode 207 as described with reference to FIGS. 17A and 17B.

Figure 18B:
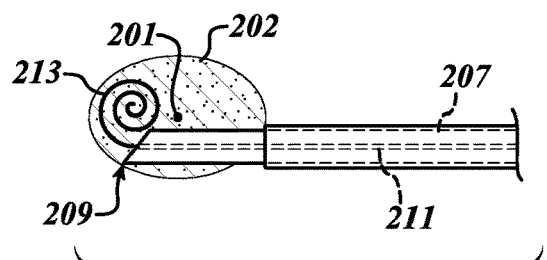

Referring to FIG. 18B, as a result of the rotation of the control handle 1160 through the rotational distance 1807, the distal end 209 of the primary electrode 207 is again extended into the target region 202 toward the distal end 213 of the secondary electrode 211. The distal end 209 of the primary electrode 207 thus resumes the position where the distal end 209 of the primary electrode 207 was situated before the distal end 209 of the primary electrode 207 was partially retracted.

Figure 19A:
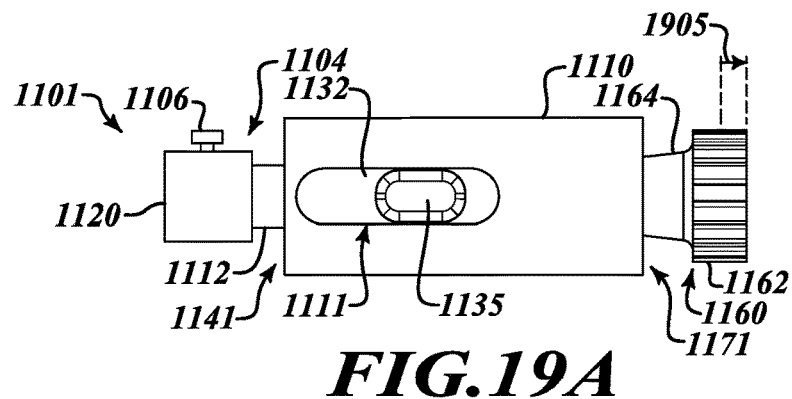
Figure 19B:
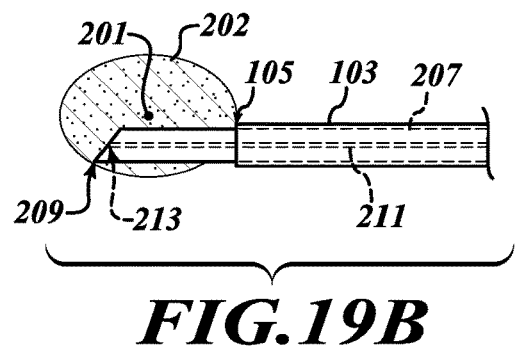

Referring to FIGS. 19A and 19B, once the primary electrode has been re-extended, the distal end 213 of the secondary electrode 211 may be retracted into the primary electrode 207. Referring to FIG. 19A, sliding the control handle 1160 through a distance 1905. The distance 1905 is of the opposite direction but an equal magnitude of the distance 1605 (FIG. 16A) through which the control handle 1160 was pushed to extend the distal end 213 of the secondary electrode. Because the control handle 1160 is engaged with the secondary actuator 1152 via the disengageable linkage formed by the insertive member 1270 of the control handle 1160 being threadably received within the recess 1265 of the secondary actuator 1252, pulling on the control handle 1160 pulls the secondary actuator 1252 through the same distance 1905.

It will be appreciated that pulling the control handle 1160 through the distance 1905 also withdraws the tapered body portion 1164 of the control handle 1160 from within the spreadable body portion 1230 of the primary actuator 1132. As a result, the insertive threads 1260 of the primary actuator 1132 are withdrawn from the receptive threads 1271 of the housing 1110. It also will be appreciated that the reextension of the distal end 209 of the primary electrode 207 described with reference to FIGS. 18A and 18B and subsequent retraction of the distal end 213 of the secondary electrode 211 were also accomplished only by moving the control handle 1160. Thus, the extension of the distal end 213 of the secondary electrode 211 (FIGS. 16A and 16B), the partial retraction of the distal end 209 of the primary electrode 207 (FIGS. 17A and 17B), the re-extension of the distal end 209 of the primary electrode 207 (FIGS. 18A and 18B), and the retraction of the distal end 213 of the secondary electrode 211 into the primary electrode 207 all were accomplished by manipulating only the control handle 1160.

Referring to FIGS. 20A and 20B, with the distal end 213 of the secondary electrode 211 withdrawn within the distal end 209 of the primary electrode 207 and the primary actuator 1132 no longer threadedly engaged with the housing 1110, the primary actuator 1132 may be manipulated to withdraw both electrodes 207 and 211 from the target region 202. Referring to FIG. 20A, the user may engage the primary actuator button 1135 to engage the primary actuator 1132 with the secondary actuator 1152, which in turn is coupled with the control handle 1160 by the insertive member 1270 of the control handle 1160 being threadably received within the orifice 1260 of the secondary actuator 1252. Then, by moving the primary actuator 1132 away from the first end 1141 of the housing through a distance 2005, the secondary actuator 1152 and the control handle 1160 are moved through the same distance 2005, and the electrodes 207 and 211 are withdrawn from the target region 202. Referring to FIG. 20B, specifically, the movement of the primary actuator 1132 and the secondary actuator 1252 through the distance 2005 withdraws the distal ends 209 and 213 of the electrodes 205 and 211, respectively, from the target region 202.

Referring to FIGS. 21A and 21B, with the electrodes 207 and 211 withdrawn from the target region 202, as desired, the sheath actuator 1104 may be engaged to withdraw the distal end 105 of the sheath 103 from adjacent the target region 202. By engaging the sheath lock 106, a user may slide the slidable sleeve 1112 out of the coupling 1120. Referring to FIG. 21B, the sliding of the slidable sleeve 1112 out of the coupling causes the distal end 105 of the sheath 103 to be withdrawn from adjacent the target region 202.

Referring to FIG. 22, an illustrative method 2200 of positioning electrodes for treatment is provided. The method 2200 starts at a block 2205. At a block 2210, a user interface operably coupled with a sheath that contains a primary electrode and a secondary electrode is positioned to move a distal end of the sheath adjacent to a target region at a first position, as described with reference to FIGS. 2, 7A-8B, 14A, and 14B. At a block 2220, a primary actuator operably coupled with the primary electrode, a secondary actuator operably coupled with the secondary electrode, and a control handle are moved in concert to a second position of the user interface to extend distal ends of the primary electrode and the secondary electrode into the target region, as described with reference to FIGS. 15A and 15B. At a block 2230, the control handle is moved in a first direction to cause the secondary actuator to move independently of the primary actuator to a third position of the user interface to extend the distal end of the secondary electrode beyond the distal end of the primary electrode, as described with reference to FIGS. 16A and 16B. At a block 2240, the control handle is moved in a second direction to cause the primary actuator to move independently of the secondary actuator to a fourth position of the user interface to partially retract the distal end of the primary electrode away from the distal end of the secondary electrode, as described with reference to FIGS. 17A and 17B. The method 2200 ends at a block 2245, with the electrodes now positioned for the administration of treatment.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
    a housing that is coupled with a sheath that contains a primary electrode and a secondary electrode, the sheath being configured to convey distal ends of the primary electrode and the secondary electrode adjacent to a target region; and
    a primary actuator operably coupled with the primary electrode;
    a secondary actuator operably coupled with the secondary electrode; and
    a control handle selectively engageable with the primary actuator and the secondary actuator, wherein the primary actuator, the secondary actuator, and the control handle are configured so that:

at a first position, the primary actuator, the secondary actuator, and the control handle are engaged to linearly slide within the housing in concert to a second position where the distal ends of the primary electrode and the secondary electrode extend into the target region;

at the second position, the control handle is slidable linearly to move the secondary actuator independently of the primary actuator in a first direction to a third position where the distal end of the secondary electrode extends beyond the distal end of the primary electrode; and at the third position, the control handle is rotatable to move the primary actuator independently of the secondary actuator in a second direction to a fourth position to partially retract the distal end of the primary electrode away from the distal end of the secondary electrode.

2. The apparatus of claim 1, wherein the housing defines receptive threads and the primary actuator defines insertive threads, wherein the receptive threads are configured to be threadedly engageable by the insertive threads upon rotation of the secondary actuator when the user interface is at the third position.

3. The apparatus of claim 2, wherein the control handle is configured so that moving the control handle from the second position to the third position causes the insertive threads to engage the receptive threads so that rotating the control handle in the second direction causes the primary actuator to move to partially retract the distal end of the primary electrode away from the distal end of the secondary electrode.

4. The apparatus of claim 3, wherein the primary actuator includes a spreadable body portion supporting the insertive threads and the control handle includes a tapered body portion configured to be inserted within the spreadable body portion of the primary actuator, such that when the control handle is moved from the second position to the third position, the tapered body of the control handle causes the spreadable body portion of the primary actuator to spread to cause the insertive threads to engage the receptive threads of the housing.

5. The apparatus of claim 3, further comprising a disengageable linkage between the control handle and the secondary actuator, wherein the disengageable linkage is configured so that:

at the third position, rotating the control handle causes the disengageable linkage to disengage the control handle from the secondary actuator to enable the control handle to move the primary actuator independently of the secondary actuator; and at the fourth position, rotating the control handle in a third direction opposite of the second direction causes the disengageable linkage to reengage the secondary actuator at the third position while causing the primary actuator to extend the distal end of the primary electrode toward the distal end of the secondary electrode.

6. The apparatus of claim 5, wherein the control handle is further configured so that:

at the fourth position, moving the control handle in a fourth direction opposite the first direction causes the secondary actuator to retract the distal end of the secondary electrode toward the distal end of the primary electrode with both the primary actuator and the secondary actuator resuming the second position; and at the second position, the primary actuator and the secondary actuator are movably engaged to move in concert to the first position where the distal ends of the primary electrode and the secondary electrode are withdrawn from the target region.

7. The apparatus of claim 1, wherein the housing includes a sheath actuator, wherein the sheath actuator includes a sheath lock, the sheath lock being configured to enable selective movement of the sheath and being further configured to enable selective locking of the sheath.

8. A system for treating tissue at a reference point, the system comprising:

a controllable electrical power source configured to selectively provide electrical power between a first pole and a second pole;

an electrosurgical apparatus configured to be inserted into a body to convey a sheath housing a primary electrode electrically coupled with the first pole of the electrical power source and a secondary electrode electrically coupled with the second pole of the electrical power source to a vicinity of a reference point; and a user interface including:

a housing that is coupled with the sheath that contains the primary electrode and the secondary electrode, the sheath being configured to convey distal ends of the primary electrode and the secondary electrode adjacent to a target region; and a primary actuator operably coupled with the primary electrode;

a secondary actuator operably coupled with the secondary electrode; and a control handle selectively engageable with the primary actuator and the secondary actuator, wherein the primary actuator, the secondary actuator, and the control handle are configured so that:

at a first position, the primary actuator, the secondary actuator, and the control handle are engaged to linearly slide within the housing in concert to a second position where the distal ends of the primary electrode and the secondary electrode extend into the target region;

at the second position, the control handle is slidable linearly to move the secondary actuator independently of the primary actuator in a first direction to a third position where the distal end of the secondary electrode extends beyond the distal end of the primary electrode; and at the third position, the control handle is rotatable to move engaged the primary actuator independently of the secondary actuator in a second direction to a fourth position to partially retract the distal end of the primary electrode away from the distal end of the secondary electrode.

9. The system of claim 8, wherein the housing defines receptive threads and the primary actuator defines insertive threads, wherein the receptive threads are configured to be threadedly engageable by the insertive threads upon rotation of the secondary actuator when the user interface is at the third position.

10. The system of claim 9, wherein the control handle is configured so that moving the control handle from the second position to the third position causes the insertive threads to engage the receptive threads so that rotating the control handle in the second direction causes the primary actuator to move to partially retract the distal end of the primary electrode away from the distal end of the secondary electrode.

11. The system of claim 10, further comprising a disengageable linkage between the control handle and the secondary actuator, wherein the disengageable linkage is configured so that:
- at the third position, rotating the control handle causes the disengageable linkage to disengage the control handle from the secondary actuator to enable the control handle to move the primary actuator independently of the secondary actuator; and
- at the fourth position, rotating the control handle in a third direction opposite of the second direction causes the disengageable linkage to reengage the secondary actuator at the third position while causing the primary actuator to extend the distal end of the primary electrode toward the distal end of the secondary electrode.

12. The system of claim 11, wherein the primary actuator includes a spreadable body portion supporting the insertive threads and the control handle includes a tapered body portion configured to be inserted within the spreadable body portion of the primary actuator, such that when the control handle is moved from the second position to the third position, the tapered body of the control handle causes the spreadable body portion of the primary actuator to spread to cause the insertive threads to engage the receptive threads of the housing.

13. The system of claim 11, wherein the control handle is further configured so that:
- at the fourth position, moving the control handle in a fourth direction opposite the first direction causes the secondary actuator to retract the distal end of the secondary electrode toward the distal end of the primary electrode with both the primary actuator and the secondary actuator resuming the second position; and
- at the second position, the primary actuator and the secondary actuator are movably engaged to move in concert to the first position where the distal ends of the primary electrode and the secondary electrode are withdrawn from the target region.

14. The system of claim 8, wherein the housing includes a sheath actuator, wherein the sheath actuator includes a sheath lock, the sheath lock being configured to enable selective movement of the sheath and being further configured to enable selective locking of the sheath.

15. A method comprising:
- positioning a user interface operably coupled with a sheath that contains a primary electrode and a secondary electrode to move a distal end of the sheath adjacent to a target region at a first position;
- sliding linearly within a housing of the user interface a primary actuator operably coupled with the primary electrode, a secondary actuator operably coupled with the secondary electrode, and a control handle in concert to a second position of the user interface to extend distal ends of the primary electrode and the secondary electrode into the target region;
- sliding linearly within the housing the control handle in a first direction to cause the secondary actuator to move independently of the primary actuator to a third position of the user interface to extend the distal end of the secondary electrode beyond the distal end of the primary electrode; and
- rotating relative to the housing the control handle to cause the primary actuator to move independently of the secondary actuator to a fourth position of the user interface to partially retract the distal end of the primary electrode away from the distal end of the secondary electrode.

16. The method of claim 15, wherein in the third position of the user interface insertive threads on the primary actuator engage receptive threads on the housing so that rotating the control handle in the second direction causes the primary actuator to move to partially retract the distal end of the primary electrode away from the distal end of the secondary electrode.

17. The method of claim 16, further comprising:
- at the fourth position, moving the control handle in a third direction opposite the second direction to resume the third position of the user interface and to cause the distal end of the primary electrode to re-extend toward the distal end of the secondary electrode;
- at the third position, moving the control handle in a fourth direction to retract the distal end of the secondary electrode toward the distal end of the primary electrode to resume the second position of the user interface; and
- at the second position, moving the primary actuator, the secondary actuator, and the control handle in concert to the first position where the distal ends of the primary electrode and the secondary electrode are withdrawn from the target region.

* * * * *

UNITED STATES PATENT AND TRADEMARK OFFICE
CERTIFICATE OF CORRECTION

PATENT NO. : 11,659,980 B2
APPLICATION NO. : 16/367151
DATED : May 30, 2023
INVENTOR(S) : Tyson et al.

Page 1 of 1

It is certified that error appears in the above-identified patent and that said Letters Patent is hereby corrected as shown below:

In the Claims

In Column 18, Line 48, in Claim 8, after "move", delete "engaged"

Signed and Sealed this
Twenty-fourth Day of September, 2024

Katherine Kelly Vidal
*Director of the United States Patent and Trademark Office*